United States Patent [19]

Kamienski et al.

[11] Patent Number: 4,678,614
[45] Date of Patent: Jul. 7, 1987

[54] HYDROCARBON-SOLUBLE ORGANOMETALLIC COMPLEXES OF MAGNESIUM AND ALKALI METALS AND METHOD OF PRODUCING SAME

[75] Inventors: Conrad W. Kamienski, Gastonia; B. Troy Dover, Kings Mountain, both of N.C.

[73] Assignee: Lithium Corporation of America, Inc., Bessemer City, N.C.

[21] Appl. No.: 803,104

[22] Filed: Nov. 27, 1985

[51] Int. Cl.$^4$ ................................................ C07F 3/02
[52] U.S. Cl. .................................. 260/665 R; 252/182
[58] Field of Search ...................................... 260/665 R

[56] References Cited

U.S. PATENT DOCUMENTS

| | | |
|---|---|---|
| 3,452,111 | 6/1969 | Kamienski et al. ............. 260/665 R |
| 3,755,478 | 8/1973 | Kamienski ...................... 260/665 R |
| 3,822,219 | 7/1974 | Kamienski et al. |
| 4,299,781 | 11/1981 | Fannin et al. .................... 260/665 R |
| 4,396,554 | 8/1983 | Robinson et al. ............... 260/665 R |

FOREIGN PATENT DOCUMENTS 1175322 12/1969 United Kingdom .
0041306 12/1981 United Kingdom .

OTHER PUBLICATIONS

J. Amer. Chem. Soc., "The Thermal Decomposition of Sodium Ethyl", vol. 51, 1929, pp. 588-593.
Journal of Organic Chemistry, "Pyrolysis of Amylsodium and the Dissociation of Organoalkali Metal Reagents to Radicals, vol. 21, 1956, pp. 93-96.
Houben-Weyl's Methoden der Organischen Chemie Band 13/1, 1970, pp. 394-404.
J. Org. Chem., "Preparation of Organometallic Complexes by Reduction of Magnesium Alkyls with Alkali Metal, vol 38, No. 21, 1973, pp. 3718-3723.

Primary Examiner—Helen M. S. Sneed
Attorney, Agent, or Firm—Bell, Seltzer, Park & Gibson

[57] ABSTRACT

Stable alkali metal trialkylmagnesiate compositions are produced in high yields by simultaneously adding to a stirred dispersion of an alkali metal in an inert liquid hydrocarbon solvent a soluble dialkylmagnesium compound and an alkyl halide. By using a 2-alkyl substituted $C_4$-$C_{18}$ primary alkyl chloride as the alkyl halide, alkali metal trialkylmagnesiates are produced which have excellent solubility, even at low temperatures, and good thermal stability over a wide range of temperatures. Moreover, the trialkylmagnesiates are soluble in liquid aliphatic or cycloaliphatic solvents in the absence of aromatic solvents or Lewis bases, which makes these compositions especially useful for certain applications, such as catalysts in anionic polymerization, where the presence of aromatic solvents or Lewis bases is undesirable.

26 Claims, No Drawings

HYDROCARBON-SOLUBLE ORGANOMETALLIC COMPLEXES OF MAGNESIUM AND ALKALI METALS AND METHOD OF PRODUCING SAME

FIELD AND BACKGROUND OF THE INVENTION

This invention relates to an improved method for preparing organometallic complexes of magnesium and alkali metals and to novel organometallic complexes of magnesium and alkali metals which are characterized by being soluble in liquid aliphatic or cycloaliphatic solvents in the absence of aromatic solvents or Lewis bases.

This invention is particularly concerned with the production of alkali metal alkyl-dialkylmagnesium compositions. Compositions of this class have been often referred to in the prior art as alkali metal alkyl-dialkylmagnesium complexes, and have been represented by the formula

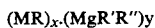

where M is lithium, sodium or potassium, and R, R' and R" are hydrocarbyl groups.

The compositions can also be described as magnesiate compositions, or more specifically alkali metal trialkylmagnesiates, and are represented by the formula

where M, R, R' and R" are as noted above, and $x+y=a+b+c$. We prefer to use the latter terminology in describing the novel compositions and process of the present invention.

Alkali metal trialkylmagnesiates of the type to which the present invention pertains are useful for various purposes, and especially as catalysts in various polymerization or telomerization reactions. For example, commonly owned U.S. Pat. No. 3,822,219 describes the use of hydrocarbon-soluble complexes of dialkylmagnesium compounds with alkyllithium compounds as initiators in the polymerization of dienes and with alkyllithium or alkylpotassium compounds as catalysts in the telomerization of conjugated dienes, such as 1,3 butadiene, to produce polymers or telomers of predictable microstructure.

Various processes have been employed for producing the alkali metal alkyl-dialkylmagnesium complexes. Malpass and Eastham, J. Org. Chem., Vol. 38, No. 21, 1973, have described a method of preparing organometallic complexes involving magnesium and alkali metals in which alkali metal is used directly to reduce a dialkylmagnesium compound to produce a dialkylmagnesium-alkali metal complex. However, in the process, part of the dialkylmagnesium is reduced to magnesium metal. Consequently, the resulting yields based upon the initial magnesium are relatively low, and the ratio of alkali metal to magnesium in the final product is less than that which would be desired. Also, in practice, it has been found that the presence of an aromatic solvent, such as benzene or toluene was necessary to maintain good solubility.

The aforementioned U.S. Pat. No., 3,822,219, describes a process illustrated by the production of a complex of a hydrocarbon soluble mixed primary alkyl-, secondary or tertiary alkylmagnesium with an alkylsodium or alkylpotassium. First a primary, linear dialkylmagnesium compound is prepared directly in a hydrocarbon solvent from magnesium metal and the corresponding alkyl halide. Then a secondary or tertiary alkyllithium is added to react the by-product magnesium halide formed in the direct preparation step. The resulting liquid solution is separated from the solid lithium chloride and the liquid solution containing a complex of a primary dialkylmagnesium with a secondary or tertiary dialkylmagnesium is then complexed with a Group I metal organic compound such as n-butylsodium.

This method requires the use of solid alkali metal alkyls, such as n-butylsodium, which are difficult to handle, and the yields obtained are somewhat lower than would be desired. Also, in all of the examples of this patent, aromatic hydrocarbons such as benzene are used to maintain the solubility of the composition in the solvent. The presence of aromatic hydrocarbons or Lewis bases (such as tertiary amines and ethers) in the complex is undesirable in certain applications, such as in anionic polymerizations, because they serve to act as chain transfer agents and/or act to decompose organometallic initiators such as alkyllithium or alkylsodium. In addition, they may require subsequent removal from the polymerization solvent.

With the foregoing in mind, it is an object of the present invention to provide an improved process for producing an alkali metal trialkylmagnesiate which provides improved yields.

It is a further object of the invention to provide an improved process as noted above which avoids loss of the expensive dialkylmagnesium reactants by reduction to magnesium metal.

Still another object of the present invention is to provide an alkali metal alkyl-dialkylmagnesium complex which is soluble in a liquid aliphatic or cycloaliphatic solvent in the absence of aromatic solvents or Lewis bases.

SUMMARY OF THE INVENTION

The improved process for producing alkali metal trialkylmagnesiates in accordance with the present invention comprises simultaneously adding to a stirred dispersion of an alkali metal in an inert liquid hydrocarbon solvent, a soluble dialkylmagnesium compound and an alkyl halide. The alkali metal alkyl is produced in high yields (e.g. 90–100%) from its corresponding alkyl halide in the presence of an equimolar quantity or less of dialkylmagnesium to form a stable, soluble alkali metal trialkylmagnesiate composition. Since the alkali metal alkyl is dissolved as it is made, the problems associated with prior processes which use difficult-to-handle solid alkali metal alkyls are avoided. Also, this process avoids loss of the expensive dialkylmagnesium compound by reduction to magnesium metal and makes it possible to produce products with high alkali metal to magnesium ratios.

A particularly advantageous and desirable aspect of the process of this invention is that it can be carried out in the absence of aromatic hydrocarbon solvents or Lewis bases, with high yields and with good stability of the resulting alkali metal trialkylmagnesiate product.

Where solubility properties are particularly important, we prefer to use as the alkyl halide a 2-alkyl substituted $C_4$–$C_{18}$ saturated acyclic primary alkyl chloride. This produces an alkali metal trialkylmagnesiate with excellent solubility, even at low temperatures, and good thermal stability over a wide range of temperatures. These compounds cannot be obtained by the prior art methods involving the direct reduction of a dialkylmagnesium with an alkali metal, since dialkylmagnesium compounds derived from 2-alkyl substituted saturated acyclic primary alkyl halides cannot be directly prepared using magnesium metal.

Thus the process of the present invention may be employed to produce a novel class of alkali metal trialkylmagnesiate compositions containing at least one 2-alkyl-substituted saturated acyclic primary alkyl group. These compositions are characterized by excellent solubility in a liquid aliphatic or cycloaliphatic solvent in the absence of aromatic solvents or Lewis bases. These compositions are especially useful in applications where the presence of aromatic hydrocarbon solvents in Lewis bases is undesirable.

The novel alkali metal trialkylmagnesiate compositions of the present invention may be represented by the formula

where
x is a number which may vary from 1 to 3;
$x = a + b + c - 2$;
M is lithium, sodium or potassium;
R is a 2-alkyl substituted $C_4$–$C_{18}$ alkyl; and
R' and R" are alkyl groups which may be the same or different, These trialkylmagnesiate compositions may be provided in the form of a solution in a solvent consisting essentially of liquid aliphatic and/or cycloaliphatic solvents in the absence of aromatic solvents or Lewis bases.

DETAILED DESCRIPTION OF THE INVENTION

In carrying out the process of the present invention, we prefer to use alkali metals in the form of finely divided dispersions in an inert hydrocarbon medium, such as mineral oil, light oil, naphthenic hydrocarbon, heptane, cyclohexane or methylcyclohexane. Dispersant media should be washed from the alkali metal before use.

The washed alkali metal is then dispersed in a solvent. Solvents suitable for use in the process of this invention may be saturated acyclic hydrocarbons, such as isopentane, n-pentane, n-heptane, or saturated cyclic hydrocarbons, such as cyclohexane or methylcyclohexane, or mixtures thereof. Aromatic hydrocarbons, such as benzene or toluene, and Lewis bases such as tertiary amines and ethers may also be employed, although in certain applications, such as in the anionic polymerization of conjugated dienes, such solvents are generally not desirable.

The process of our invention involves the simultaneous addition of both the alkyl halide and dialkylmagnesium compound to the moderately-stirred alkali metal dispersion. We have found that it is quite important that these compounds be simultaneously added to the alkali metal dispersion. The addition of all the dialkylmagnesium compound to the alkali metal dispersion prior to start up of the alkyl halide feed causes the alkali metal particles to agglomerate and thus to become much less effective in forming the alkali metal alkyl. Addition of too much of the dialkylmagnesium compound during the alkyl halide feed causes the formation and precipitation of a sticky form of the alkali metal alkyl-dialkylmagnesium complex (one alkali metal per two magnesiums), which once again prevents the alkali metal from efficiently reacting with the alkyl halide. Addition of the dialkylmagnesium compound at or near the end of the alkyl halide addition does not promote the formation of high yields of alkali metal alkyl, nor of a light colored product solution due to side reactions associated with the alkali metal alkyl, such as coupling or disproportionation reactions with alkyl halide or thermal degradation (indicated by deep color formation).

The reaction may be carried out at temperatures from well below 0° C. to about the boiling point of the solvents, but the reaction proceeds quite well in the moderate temperature range of about 25° to 35° C.

In our preferred procedure, separate addition funnels for the alkyl halide and the dialkylmagnesium are employed. Addition of the alkyl halide to the alkali metal dispersion is begun first to initiate the reaction. After about 10% of the alkyl halide has been added, the dialkylmagnesium solution addition is begun gradually (dropwise) at such a rate as to complete its addition at about the same time that the alkyl halide addition is completed. For a one mole run, an overall addition time of about 1–1¼ hours is exemplary. A normal post-reaction stirring period of about 1 to 2 hours is then carried out, but is probably not necessary. Excellent results have also been observed where the alkyl halide and dialkylmagnesium solutions are first mixed together and then slowly added to the reactor.

Examples of alkyl halides which may be used in the process of this invention are n-butyl chloride, n-butyl bromide, n-hexyl chloride, n-octyl chloride, n-hexyl bromide, and 2-ethylhexyl chloride.

Examples of suitable dialkylmagnesium compounds are n-hexylethylmagnesium, n-butyl-sec-butylmagnesium, di-n-hexylmagnesium, n-butylethylmagnesium and n-butyl-n-octylmagnesium. Most preferable are n-butyl-sec-butylmagnesium and n-butyl-n-octylmagnesium. The dialkylmagnesium compounds can be prepared by known methods, such as for example from Grignard reagents.

In carrying out the process, we prefer to employ an excess (e.g. up to about 40–45%) of the alkali metal in its reaction with alkyl halide and to control the molar ratio of the alkali metal to magnesium in the resulting product by limiting the amount of dialkylmagnesium compound.

In the product, the molar ratio of the alkali metal and dialkylmagnesium compound may be varied over a wide range to produce alkali metal alkyl-dialkylmagnesium complexes with various ratios of alkali metal to magnesium. Best yields and solubilities are observed at a molar ratio of alkali metal to dialkylmagnesium compounds of about 1:1. At ratios significantly less than 1:1, the results produce two immiscible liquid phases, but the phases may be redispersed by addition of a Lewis base, such as triethylamine. As the ratio is increased above 1:1, yields of the resulting alkali metal alkyl are somewhat reduced. We prefer to maintain the molar ratio within the range of about 1:1 to about 3:1, and the most favored ratios are from about 1:1 to 1.5:1.

The following Examples illustrate various aspects of our invention, show how the process may be practiced and describe various soluble, stable alkali metal trialkylmagnesiates in accordance with the invention. Although specific procedures and reactants are described in these Examples, it will be understood that these are provided for purposes of illustration and are not to be regarded as limiting the scope of the present invention. Persons skilled in the appropriate arts will recognize that other novel alkali metal trialkylmagnesiate compositions can be made pursuant our invention and that different procedures, reaction conditions, solvents, and reactants can be employed in our novel process without departing from the teachings and principles disclosed herein.

EXAMPLE 1

Preparation of Sodium 2-Ethylhexyl-, n-Butyl-, sec-Butylmagnesiate

A dispersion of sodium metal (3.26 moles, 40% in mineral oil) was transferred under argon and diluted with hexane, then filtered through a medium frit filter funnel. Two small hexane washes followed by a cyclohexane wash were used to thoroughly wash oil from the metal.

After washing, the sodium metal was slurried in the reacting solvent (1 liter cyclohexane) and transferred to a reactor vessel equipped with a mechanical stirrer, thermometer, two addition funnels, and argon gas purge. One liter of isopentane was then added, and 1.35 moles 2-ethylhexyl chloride was weighed and transferred to the first addition funnel. 1.08 moles of dibutylmagnesium (DBM) was weighed and transferred to the second addition funnel. Several ml (1-3) of 2-ethylhexyl chloride was added to the moderately stirred dispersion to initiate reaction. The reaction initiated very quickly and the reaction temperature was maintained between 30°-35° C., cortrolling with halide feed rate and Dry Ice hexane bath.

When approximately 10% of the halide feed was reacted, the DBM feed was started and adjusted to finish just shortly after the halide feed is completed. The total feed time was about 1 to 1¼ hours. A post reaction time of one to one and one half hours was given before filtration was begun. The product mixture (dark gray-blue) was then filtered through a medium frit filter using filter aid and then several small cyclohexane washes were used to thoroughly wash the muds. Filtration rate was very good (1 liter in about 30 mins.). The product solution was analyzed for total base, Mg (EDTA titration) and Na (AAS).

The recovered solution was stable to color change and precipitation at room temperature and at refrigerator temperatures (0°-5° C.) over extended periods of time (several months).

EXAMPLES 2-9

The procedure employed in Example 1 above was used in a series of runs to prepare 1:1 alkylsodium-dialkylmagnesium complexes utilizing various alkylsodiums, such as 2-ethylhexylsodium, n-hexylsodium, and n-octylsodium, and various dialkylmagnesiums such as n-butyl-sec-butylmagnesium, n-butylethylmagnesium, and n-butyl-n-octylmagnesium.

The recovered solutions varied in color from light yellow to deep amber, and were analyzed for magnesium by EDTA titration and for sodium by AAS. The results of the respective runs are presented in Table I.

Best results were obtained with 2-ethylhexylsodium and dibutylmagnesium and especially when the dibutylmagnesium was added gradually to the reaction mixture after about 10%-50% of the halide feed had been added. Yields of 2-ethylhexylsodium prepared in this way were better (about 10% or more) than when no dibutylmagnesium was present (see Comparison Example A below and Table II). Lighter-colored product solutions were obtained, also, indicating the improved stability of 2-ethylhexylsodium in the complex. When n-hexyl or n-octyl chlorides were substituted for 2-ethylhexyl chloride, yields of the corresponding alkylsodium were high (90+%), but the product solution could not be as readily filtered from the finely divided by-product halide salt. The yield for these latter runs was estimated.

When n-butylethylmagnesium (Example 6) (Example 7) was substituted for dibutylmagnesium, the yields of 2-ethylhexylsodium were lower than when dibutylmagnesium was used and in the case of n-butylethylmagnesium, solids precipitated during the reaction, but could be solubilized by the addition of triethylamine.

COMPARISON EXAMPLE A -

PREPARATION OF 2-ETHYLHEXYLSODIUM

A procedure similar to that described above was used to prepare 2-ethylhexylsodium (2-EHS) directly from sodium metal and 2-ethylhexyl chloride. The sodium dispersion was washed and added to the reaction vessel along with an inert hydrocarbon solvent. 2-Ethylhexyl chloride and solvent was charged to the addition funnel and added gradually to the sodium dispersion. The product was then filtered, the muds washed with cyclohexane, and the recovered solution was titrated and the yield, based on the halide, was determined. The results of several comparative runs are set forth in Table II below.

TABLE II

| Comparative Example | 2-Ethylhexylsodium Preparations | | | | | | |
|---|---|---|---|---|---|---|---|
| | Na Metal | | | EHC | | Filtrate | % |
| | Moles | % Excess | Solvent | Moles | Color | Na(M) | Yield |
| A1 | 0.605 (a) | 40 | MCHX (b) Isopent | 0.216 | Army Green | 0.89 | 80.6 |
| A2 | 0.652(a) | 40 | Cyclo. | 0.232 | Very dark brown | 0.64 | 80 |

(a) Na dispersion (40% in mineral oil) similar to Example 1-9.
(b) MCHX = Methylcyclohexane The product mixes generally filtered quite well to give clear, but usually dark amber to brown filtrates, which deepened still further to opaque brown solutions overnight, even under refrigeration. In some cases, a small amount of solids also formed during this time. The yields observed correspond closely to the results of the 2-ethylhexylsodium preparations reported by Eidt and Malpass in published European Patent Application EP No. 0041306.

EXAMPLES 10-18

Runs were carried out at RNa/R'R"Mg ratios other than 1.0 to examine other useful Na/Mg ratios. The results of these runs are shown in Table III.

Using a similar procedure to that employed in Example 1, it was found that yields of 2-ethylhexylsodium (2-EHS) were generally lower at the other ratios attempted. This was borne out by the lower than expected Na/Mg (1.5-2.0) ratios in the final product solutions. Yields of 2-EHS made in the presence of considerably less than a sufficient quantity of DBM to give a Na/Mg ratio of about 1.0 are generally lower and are approximately equal to yields of 2-EHS made in the absence of DBM (60–80%).

The stability of such $Na_xMgR_xR'R''$ solutions ($x > 1.0$) is not as good as that of NaMgRR'R" solutions ($x = 1.0$). Solutions are darker colored and solids precipitate from solution on standing.

The yield and color of these 2-ethylhexylsodium complexes with Na/Mg > 1 can be improved by carrying out the reaction of sodium dispersion with 2-ethylhexyl chloride in the presence of preformed sodium n-butyl-sec-butyl-2-ethylhexyl magnesiate instead of dibutylmagnesium (see run 10 of Table III).

As noted in the preceding section, gross precipitation occurs with BEM in place of DBM during reaction to form 2-EHS. This occurs at higher Na/Mg ratios as well (see Example 15). One run (Example 16) was made in which sufficient DBM was added to provide a final Na/Mg ratio less than 1.0 (0.8). Two liquid phases resulted, requiring the addition of triethylamine to effect total dissolution of the phases. However, resulting yield of 2-EHS was good.

TABLE I

NaMgRR'R" Preparations

| Example | Moles | Na Metal % Excess | Moles EHC (a) | Moles DBM (b) | Color | Conc. of Product Mg(M) | Na(M) | Na/Mg Ratio | Yield (%) |
|---|---|---|---|---|---|---|---|---|---|
| 1 | 3.26 | 20 | 1.35 | 1.08 | Yellow Amber | 0.54 | 0.62 | 1.15 | 91 |
| 2 | 3.04 | 20 | 1.27 | 1.02 | Yellow Amber | 0.57 | 0.64 | 1.12 | 91 |
| 3 | 0.826 | 50 | 0.232 | 0.1856 | Orange Clear | 0.49 | 0.53 | 1.08 | 94 (c) |
| 4 | 0.896 | 45 | 0.232 | 0.1856 | Light Yellow | 0.43 | 0.50 | 1.16 | 93 (d) |
| 5 | 0.809 | 20 | 0.337 (e) | 0.2696 | Amber | 0.55 | 0.63 | 1.15 | 92 (f) |
| 6 | 0.786 | 20 | 0.3275 | 0.262 (g) | Light Yellow | 0.42 | 0.42 | 1.0 | 80 (h) |
| 7 | 0.8348 | 20 | 0.3478 | 0.3319 (i) | — | 0.43 | 0.41 | .95 | 90 |
| 8 | 0.883 | 45 | 0.232 | 0.1856 | Light Yellow | 0.44 | 0.49 | 1.12 | 100 |
| 9 | 0.652 | 20 | 0.273 (j) | 0.218 | Yellow | 0.66 | 0.77 | 1.16 | 93 (f) |

(a) ethylhexyl chloride
(b) dibutylmagnesium
(c) began DBM feed after 50% EHC added
(d) began DBM feed after 10% EHC added
(e) n-hexyl chloride
(f) unable to filter all of solution-yield estimated
(g) n-butylethylmagnesium (BEM)
(h) triethylamine added to dissolve solids
(i) n-butyl n-octylmagnesium (BOM)
(j) n-octyl chloride

TABLE III

$Na_xMgR_xR'R''$ Preparations

| Example | Expected Product | Moles | Na % Excess | EHC (a) Moles | DBM Moles | Color | Analysis Mg(M) | Na(M) | Na/Mg Ratio | % Yield RNa |
|---|---|---|---|---|---|---|---|---|---|---|
| 10 | $Na_2MgR_4$ | 0.274 | 93 | 0.1141 | 0.1426 (b) | Green | 0.22 | 0.38 | 1.73 | 91 (c) |
| 11 | $Na_2MgR_4$ | 1.12 | 40 | 0.40 | 0.16 | Amber | 0.21 | 0.33 | 1.57 | 63 |
| 12 | $Na_2MgR_4$ | 0.9782 | 20 | 0.4076 | 0.1631 | Dark Amber | 0.29 | 0.59 | 2.03 | 81 |
| 13 | $Na_2MgR_4$ | 0.9826 | 30 | 0.3779 | 0.3023 | — | 0.32 | 0.57 | 1.78 | 71 |
| 14 | $Na_2MgR_4$ | 0.891 | 20 | 0.371 | 0.1484 | Dark red | 0.31 | 0.53 | 1.71 | 68 |
| 15 | $Na_2MgR_4$ | 1.00 | 20 | 0.417 | 0.334 (d) | Yellow | 0.20 | 0.29 | 1.45 | 33 (e) |
| 16 | $Na_{0.8}MgR_{2.8}$ | 0.783 | 20 | 0.326 | 0.326 | Yellow | 0.57 | 0.51 | 0.89 | 90 (f) |
| 17 | $Na_{2.5}MgR_{4.5}$ | 0.6087 | 20 | 0.2536 | 0.1014 | Dark Red | 0.24 | 0.43 | 1.79 | 71 |
| 18 | $Na_{1.5}MgR_{3.5}$ | 0.696 | 20 | 0.2898 | 0.1545 | Yellow | 0.28 | 0.43 | 1.54 | 83 |

(a) ethylhexyl chloride
(b) $NaMgR_3$ from prior run (Ex. 9) used in place of DBM.
(c) yield estimated
(d) n-butylethylmagnesium (BEM).
(e) Yields poor due to precipitation of product.
(f) Two liquid phases formed; required addition of triethylamine to dissolve.

EXAMPLE 19

Stability of NaMgRR'R"

The product produced in Example 2 above was adjusted to exactly 1:1 Na/Mg by addition of dibutylmagnesium and the stability was measured at various temperatures after 12 and 24 days using several analytical procedures as set forth in Table IV.

TABLE IV

| | | Titration Total Base (N) | NaMgRR'R" Stability | | | | | |
|---|---|---|---|---|---|---|---|---|
| | | | Atomic Absorption | | | Active Alkyl (N) | | Residual Alkalinity |
| | | | Mg (M) | Mg (M) | Na (M) | Watson | Eastham | |
| Day 1 | | 1.84 | 0.63 | 0.64 | 0.64 | — | — | — |
| Day 12 | 0° C. | 1.88 | 0.64 | 0.68 | 0.63 | — | — | — |
| | 20° C. | 1.85 | 0.67 | 0.68 | 0.65 | — | — | — |
| Day 24 | 0° C. | 1.83 | 0.64 | 0.63 | 0.62 | 1.86 | | none |
| | 20° C. | 1.86 | 0.64 | 0.64 | 0.64 | 1.84 | | 1.0 |

This example demonstrates the stability of 1:1 sodium tributylmagnesiates of the present invention over a broad range of temperatures.

That which is claimed is:

1. A process for preparing an alkali metal trialkylmagnesiate comprising simultaneously adding to a stirred dispersion of an alkali metal in an inert liquid hydrocarbon solvent a soluble dialkylmagnesium compound and a 2-alkyl substituted $C_4$–$C_{18}$ primary alkyl halide.

2. A process according to claim 1 wherein the mole ratio of the alkyl halide to dialkylmagnesium compound is maintained within the range of from about 1:1 to about 3:1.

3. A process according to claim 1 wherein the alkyl halide comprises a 2-alkyl substituted $C_4$–$C_{18}$ primary alkyl chloride.

4. A process according to claim 1 wherein the dialkylmagnesium compound is a $C_4$–$C_{18}$ dialkylmagnesium.

5. A process according to claim 1 wherein the inert liquid hydrocarbon solvent consists essentially of an aliphatic and/or cycloaliphatic solvent.

6. A process according to claim 1 comprising the step of initially adding up to about 10 percent of the total alkyl halide to the stirred dispersion to initiate the reaction, and thereafter simultaneously adding the dialkylmagnesium compound and the remaining alkyl halide.

7. A process for preparing a sodium trialkylmagnesiate comprising simultaneously adding to a stirred dispersion of sodium in an inert liquid hydrocarbon solvent a soluble dialkylmagnesium compound and 2-ethylhexyl chloride.

8. A process for preparing an alkali metal trialkylmagnesiate which is soluble in a liquid aliphatic or cycloaliphatic solvent in the absence of aromatic solvents or Lewis bases, comprising simultaneously adding to a stirred dispersion of an alkali metal in an inert liquid solvent consisting essentially of aliphatic and/or cycloaliphatic solvents, in a molar ratio of about 1:1 to about 3:1, a soluble dialkylmagnesium compound and a 2-alkyl substituted $C_4$–$C_{18}$ primary alkyl chloride, and thereafter separating the soluble alkali metal trialkylmagnesiate from the remaining solids.

9. A process according to claim 8 wherein said dialkylmagnesium compound comprises n-butyl-sec-butylmagnesium.

10. A process according to claim 8 wherein said alkali metal is sodium and said 2-alkyl substituted $C_4$–$C_{18}$ primary alkyl chloride is 2-ethylhexyl chloride.

11. A process for preparing an alkali metal alkylmagnesiate comprising reacting a dispersion of alkali metal with a 2-alkyl substituted $C_4$–$C_{18}$ primary alkyl chloride in the presence of an alkali metal trialkylmagnesiate.

12. A process according to claim 11 wherein the ratio of the total alkali metal in the reactants to magnesium is greater than 1.

13. A process according to claim 11 wherein said alkali metal is sodium and said alkyl chloride is 2-ethylhexyl chloride.

14. A composition which is soluble in a liquid aliphatic or cycloaliphatic solvent in the absence of aromatic solvents or Lewis bases, comprising a mixture of an alkylmetallic compound of magnesium and at least one alkylmetallic compound of an alkali metal, the alkyl radical of at least one of said alkylmetallic compounds comprising a 2-alkyl substituted primary alkyl group of four or more carbon atoms.

15. A composition according to claim 14 wherein the remaining alkyl radicals of said alkylmetallic compounds comprise $C_4$ to $C_{18}$ alkyls.

16. A composition according to claim 14 wherein said alkylmetallic compound of magnesium comprises a dialkylmagnesium compound.

17. A composition according to claim 14 wherein the mole ratio of said alkylmetallic compound of magnesium to said at least one alkylmetallic compound of an alkali metal is from about 1:1 to about 1:3.

18. A composition according to claim 14 wherein said alkylmetallic compound of magnesium is dibutylmagnesium and said alkylmetallic compound of an alkali metal is 2-ethylhexylsodium.

19. An alkali metal trialkylmagnesiate of the formula $$M_xMgR_aR'_bR''_c$$

where x is a number which may vary from 1 to 3;

x = a + b + c − 2;

M is lithium, sodium or potassium;

R is a 2-alkyl substituted $C_4$–$C_{18}$ primary alkyl group; and

R' and R" are alkyl groups which may be the same or different, said trialkylmagnesiate being in the form of a solution in a solvent consisting essentially of liquid aliphatic and/or cycloaliphatic solvents.

20. A composition according to claim 19 wherein R' and R" are $C_4$–$C_{18}$ hydrocarbyl groups.

21. An alkali metal trialkylmagnesiate composition which is soluble in a liquid aliphatic or cycloaliphatic solvent in the absence of aromatic solvents or Lewis bases and which is prepared by simultaneously adding to a stirred dispersion of an alkali metal in an inert liquid aliphatic and/or cycloaliphatic solvent a soluble dialkylmagnesium compound and a 2-alkyl substituted $C_4$–$C_{18}$ primary alkyl halide.

22. A composition according to claim 21 wherein the mole ratio of the alkyl halide to dialkylmagnesium compound ranges from about 1:1 to about 3:1.

23. A composition according to claim 21 wherein the alkyl halide comprises a 2-alkyl substituted $C_4$–$C_{18}$ primary alkyl chloride.

24. A composition according to claim 21 wherein the dialkylmagnesium is dibutylmagnesium and the alkyl halide is 2-ethylhexyl chloride.

25. A process according to claim 8 wherein said dialkylmagnesium compound comprises n-butyl-n-octylmagnesium.

26. A composition according to claim 21 wherein said dialkylmagnesium compound comprises n-butyl-n-octylmagnesium and the alkyl halide is 2-ethylhexyl chloride.

* * * * *